(12) United States Patent
Singh

(10) Patent No.: US 11,647,920 B2
(45) Date of Patent: May 16, 2023

(54) SYSTEMS AND METHODS FOR MEASUREMENT OF ANATOMIC ALIGNMENT

(71) Applicant: MiRus LLC, Marietta, GA (US)

(72) Inventor: Angad Singh, Marietta, GA (US)

(73) Assignee: MiRus LLC, Marietta, GA (US)

( * ) Notice: Subject to any disclaimer, the term of this patent is extended or adjusted under 35 U.S.C. 154(b) by 574 days.

(21) Appl. No.: 16/647,074

(22) PCT Filed: Sep. 17, 2018

(86) PCT No.: PCT/US2018/051328
§ 371 (c)(1),
(2) Date: Mar. 13, 2020

(87) PCT Pub. No.: WO2019/055912
PCT Pub. Date: Mar. 21, 2019

(65) Prior Publication Data
US 2020/0221974 A1 Jul. 16, 2020

Related U.S. Application Data

(60) Provisional application No. 62/559,093, filed on Sep. 15, 2017.

(51) Int. Cl.
*A61B 5/00* (2006.01)
*A61B 5/107* (2006.01)
(Continued)

(52) U.S. Cl.
CPC .......... *A61B 5/1071* (2013.01); *A61B 5/0024* (2013.01); *A61B 5/4528* (2013.01);
(Continued)

(58) Field of Classification Search
CPC ... A61B 5/1071; A61B 5/0024; A61B 5/4528; A61B 5/4561; A61B 5/6878;
(Continued)

(56) References Cited

U.S. PATENT DOCUMENTS 9,138,319 B2 * 9/2015 Fanson ................. A61B 34/20
2013/0322726 A1 12/2013 Nathaniel
(Continued)

FOREIGN PATENT DOCUMENTS

WO 2016/154430 A1 9/2016

OTHER PUBLICATIONS

International Search Report and Written Opinion issued in corresponding application No. PCT/US2018/051328, dated Dec. 6, 2018, 12 pages.
(Continued)

*Primary Examiner* — May A Abouelela
(74) *Attorney, Agent, or Firm* — Meunier Carlin & Curfman LLC

(57) ABSTRACT

Systems and methods for estimating anatomic alignment between two or more bones are described herein. An example method can include registering an anatomic reference frame. Additionally, the method can include establishing a respective rotational relationship between each of one or more bones and an orientation sensor attached to each of the one or more bones. The method can also include receiving, from each of the orientation sensors, orientation information, and then calculating an orientation of a bone relative to the anatomic reference frame. The method can further include calculating, using the respective orientations of the bones relative to the anatomic reference frame, an anatomic alignment parameter between first and second bones.

27 Claims, 8 Drawing Sheets

(51) Int. Cl.
*A61B 34/00* (2016.01)
*A61B 90/00* (2016.01)
*A61B 34/10* (2016.01)
*A61B 34/20* (2016.01)

(52) U.S. Cl.
CPC .......... *A61B 5/4561* (2013.01); *A61B 5/6878* (2013.01); *A61B 34/25* (2016.02); *A61B 90/37* (2016.02); *A61B 5/6882* (2013.01); *A61B 5/6884* (2013.01); *A61B 2034/105* (2016.02); *A61B 2034/2048* (2016.02); *A61B 2034/2068* (2016.02); *A61B 2090/365* (2016.02); *A61B 2090/376* (2016.02); *A61B 2505/05* (2013.01); *A61B 2562/0219* (2013.01)

(58) Field of Classification Search
CPC ....... A61B 34/25; A61B 90/37; A61B 5/6882; A61B 5/6884; A61B 2034/105; A61B 2034/2048; A61B 2034/2068; A61B 2090/365; A61B 2090/376; A61B 2505/05; A61B 2562/0219; A61B 5/4566; A61B 34/20; A61B 5/002; A61B 5/1121; A61B 2090/502; A61B 5/4571; A61B 5/4576; A61B 5/4585; A61B 2034/2065; A61B 2090/372; A61B 2090/067
See application file for complete search history.

(56) References Cited

U.S. PATENT DOCUMENTS

| | | | | |
|---|---|---|---|---|
| 2014/0114179 A1* | 4/2014 | Muller | ................... | A61B 34/20 600/424 |
| 2014/0225999 A1* | 8/2014 | Bracke | ................... | A61B 34/10 348/77 |
| 2014/0253712 A1 | 9/2014 | Vilsmeier et al. | | |
| 2014/0257309 A1* | 9/2014 | Aram | ................... | A61F 2/3859 606/88 |
| 2014/0275815 A1* | 9/2014 | Stein | ................... | A61B 5/4528 600/300 |
| 2014/0277542 A1* | 9/2014 | Stein | ................... | A61F 2/4657 623/20.32 |
| 2015/0073426 A1* | 3/2015 | Ross | ................... | A61B 17/56 606/102 |
| 2015/0142372 A1* | 5/2015 | Singh | ................... | A61B 5/1071 702/150 |
| 2015/0164657 A1* | 6/2015 | Miles | ................... | A61B 90/13 700/98 |
| 2015/0238271 A1* | 8/2015 | Wollowick | ................ | G06T 7/33 382/128 |
| 2016/0007909 A1 | 1/2016 | Singh et al. | | |
| 2016/0100909 A1* | 4/2016 | Wollowick | ............ | G06T 7/0014 600/424 |
| 2016/0220318 A1* | 8/2016 | Falardeau | .............. | A61B 34/10 |
| 2016/0242934 A1* | 8/2016 | van der Walt | ........ | A61F 2/4657 |
| 2016/0360997 A1 | 12/2016 | Yadav et al. | | |
| 2017/0007328 A1* | 1/2017 | Cattin | ................... | A61B 34/10 |
| 2017/0086674 A1* | 3/2017 | Keefer | ................. | A61B 5/4504 |
| 2017/0224422 A1* | 8/2017 | Bakirtzian | ........... | A61B 5/1079 |
| 2017/0231709 A1 | 8/2017 | Gupta et al. | | |
| 2017/0273746 A1* | 9/2017 | Flexman | ................ | A61B 5/1128 |
| 2017/0325892 A1* | 11/2017 | Aghazadeh | ............... | A61F 2/34 |
| 2018/0085135 A1* | 3/2018 | Singh | ................. | A61B 17/1707 |
| 2018/0289426 A1* | 10/2018 | Dace | ................... | A61B 34/20 |
| 2018/0289429 A1* | 10/2018 | Roger | ................... | A61B 34/20 |
| 2018/0296133 A1* | 10/2018 | Brack | ................... | A61B 5/1127 |
| 2018/0311051 A1* | 11/2018 | Donaldson | ............ | A61B 34/20 |
| 2019/0090952 A1* | 3/2019 | Bonny | ................... | A61B 34/25 |
| 2019/0133498 A1* | 5/2019 | Vissiere | ............... | A61B 5/1124 |
| 2019/0201155 A1* | 7/2019 | Gupta | ................... | G06T 7/33 |

OTHER PUBLICATIONS

Extended European Search Report issued in corresponding application No. EP 18855542, dated May 11, 2021, 8 pages.

* cited by examiner

SYSTEMS AND METHODS FOR MEASUREMENT OF ANATOMIC ALIGNMENT

CROSS-REFERENCE TO RELATED APPLICATIONS

This is a national stage application of PCT International Application No. PCT/US2018/051328, filed on Sep. 17, 2018, entitled "Systems and Methods for Measurement of Anatomic Alignment," which claims priority to, and the benefit of, U.S. provisional patent application No. 62/559,093, filed on Sep. 15, 2017, and entitled "SYSTEMS AND METHODS FOR MEASUREMENT OF ANATOMIC ORIENTATION," the disclosures of which are expressly incorporated herein by reference their entireties.

TECHNICAL FIELD

The present disclosure relates generally to orthopedic surgery including, but not limited to, joints, spine, upper and lower extremities, and maxillofacial surgery, more particularly, to systems and methods for measuring anatomic alignment.

BACKGROUND

Many orthopedic surgeries, such as those involving the spine, knee, or hip are complex procedures that require a high degree of precision in achieving the desired surgical objectives including achievement of anatomic alignment. Compounding the problem is limited surgical exposure and visibility, particularly in the case of minimally invasive procedures. Consequently, the risk of not achieving surgical objectives including anatomic alignment is high. Anatomic alignment parameters including, but not limited to, joint angles (e.g., hip-knee-ankle angle), spine alignment angles (e.g., Cobb angles in coronal and/or sagittal planes such as Lordosis, Kyphosis), etc., are important parameters related to prosthetic placement and therefore monitoring anatomic alignment in three dimensions during the surgical procedure is advantageous and assists in attainment of the surgical goal.

Currently, many orthopedic surgeons intra-operatively evaluate anatomic alignment using an imprecise combination of subjective experience of the surgeon, rudimentary mechanical instrumentation, and/or intra-operative imaging involving the use ionizing radiation. Intra-operative imaging in particular may be relied on heavily in the case of minimally invasive surgeries involving complex anatomies, such as spine surgery. However, the intra-operative imaging is typically not conducted in real-time, not three dimensional (3D), lacks precision, and/or has to be repeated whenever there is movement of the anatomy and/or surgical instrument thereby increasing exposure of the patient and surgical team to harmful radiation over the duration of the surgical procedure.

Because existing techniques for assessing intra-operative anatomic alignment are extremely subjective and/or imprecise, the performance of the corrected anatomy is highly variable and dependent on the experience level of the surgeon. Perhaps not surprisingly, it is difficult for patients and doctors to reliably predict the relative success of the surgery (and the need for subsequent corrective/adjustment surgeries) until well after the initial procedure. Such uncertainty has a negative impact on long term clinical outcomes, patient quality of life, and the ability to predict and control costs associated with surgery, recovery, and rehabilitation.

Some computer-assisted surgical systems may provide a platform for more reliably estimating anatomic alignment. These systems typically require complex tracking equipment, bulky markers/sensors, line of sight issues due to optical nature of the tracking, time-consuming instrument calibration/registration procedures that need repeating during the procedure, and highly-specialized software packages that often require technical support personnel to work with doctor in the operating room. Not only do such systems tend to be costly, these systems also tend to be far too complex to warrant broad adoption among orthopedic surgeons. Moreover, the size of the trackers used make these systems unsuitable for measurement of alignment of smaller bones such as spinal vertebrae.

The presently disclosed systems and associated methods for measuring anatomic alignment are directed at overcoming one or more of the problems set forth above and/or other problems in the art.

SUMMARY

Systems and methods for estimating anatomic alignment are described herein. As described below, the systems and methods can optionally be used during a surgical procedure (e.g., intra-operative estimation of anatomic alignment).

According to one aspect, the present disclosure is directed to a method for estimating alignment between two or more bones in one or more reference anatomic planes. The method may comprise registration of one or more anatomic reference planes or axes. For example, in a spine surgery with the patient in prone or lateral position, the method may comprise receiving, from an orientation sensor, information indicative of the orientation of a first anatomic axis established between two pelvic landmarks such as the left and right posterior superior iliac spines. If the patient is in supine position, left and right anterior superior iliac spines may be utilized instead. The method may further comprise calculating an orientation of an anatomic plane, where the anatomic plane is perpendicular to the first anatomic axis and represents the orientation of the sagittal plane of the body. Alternatively or additionally, the method may further comprise receiving, from the orientation sensor, information indicative of the orientation of a second anatomic axis that is not parallel to the first anatomic axis established between at least one of the two pelvic landmarks and a third landmark such as the spinous process of a vertebrae. The method may further comprise calculating an orientation of a second anatomic plane containing the first and second anatomic axes, the second anatomic plane representing the orientation the coronal plane of the body. Alternatively, the method may comprise receiving, from the orientation sensor, orientation of a third anatomic plane containing a first, second, and third landmarks, the third anatomic plane representing the orientation of the coronal plane of the body. The method can be extended to register additional anatomic planes and/or axes so long as suitable anatomic landmarks are available and/or geometric relationship with previously registered planes and/or axes are known. For example, orientation of the transverse or axial plane can be registered concurrent to the sagittal and coronal planes since the transverse or axial plane is orthogonal to both the sagittal and coronal planes.

In some implementations, the method further comprises coupling orientation sensors to one or more bones and registering anatomic reference planes and/or axes by moving bones in one or more anatomic reference planes or around one or more anatomic reference axes. The method further comprises establishing/registering the rotational relationship between the sensor and the respective bone. The method furthers comprises receiving from one or more orientation sensors coupled to one or more respective bones, information indicative of orientation relative to one or more anatomic planes or axes and alignment between two or more bones in one or more anatomic planes.

In accordance with another aspect, the present disclosure is directed to a system for estimating alignment between two or more bones in one or more anatomic reference planes. The system comprises an elongated tool having an orientation sensor coupled to the tool. The orientation sensor is configured to detect information indicative of an orientation of the tool. The system also comprises a processor, communicatively coupled to the tool's orientation sensor and configured to receive information indicative of the orientation of the elongated tool such as in a first position, the first position configured to estimate the orientation of a first anatomic axis established between two anatomical landmarks such as the left and right posterior superior iliac spines of a patient's pelvis in prone or lateral position. If the patient is in supine position, left and right anterior superior iliac spines may be utilized instead. The processor may also be configured to calculate an orientation of one or more anatomic planes or axes based on the estimated tool orientations such as the sagittal plane that is orthogonal to the first anatomic axis. The processor may be further configured to receive information indicative of the orientation of the elongated tool in other positions such as a position configured to estimate the orientation of a second anatomic axis established between at least one of the estimated positions of the left and right posterior superior iliac spines and a third landmark such as the spinous process of a vertebra. The processor may be further configured to calculate the orientation of a second anatomic plane based, at least in part, on the above first and second anatomic axis such as the coronal plane that is parallel to the second anatomic plane containing the above axes. Alternatively, the processor may be further configured to receive information indicative of the orientation of a third anatomic plane that is parallel to a plane containing the three landmarks above, the third anatomic plane representing the coronal plane. The processor may also be configured to calculate an orientation of anatomic planes or axes based, at least in part, on the previously estimated anatomic axes or planes. The processor may further be configured to calculate orientation of additional anatomic planes and/or axes so long as suitable anatomic landmarks are available and/or geometric relationship with previously registered planes and/or axes are known. For example, orientation of the transverse or axial plane can registered concurrent to the sagittal and coronal planes since the transverse or axial plane is orthogonal to both the sagittal and coronal planes. The system also comprises one or more orientation sensors coupled to one or more bones with the processor configured to receive information indicative one or more anatomic planes and/or axes based on the movement of the bones in or more anatomic planes or around one or more anatomic axes. The process may further be configured to receive information indicative of the rotational relationship between the sensors and its respective bone. The processor may be further configured to receive information indicative of orientation of one or more bones relative to one or more anatomic planes or axes and alignment between two or more bones in one or more registered anatomic reference planes.

An example method for estimating anatomic alignment between two or more bones is described herein. The method can include receiving, via an orientation sensor, first information indicative of an orientation of an anatomic axis or plane relative to a global reference frame; registering, using the first information, an anatomic reference frame; establishing a rotational relationship between respective reference frames of an orientation sensor attached to a first bone and the first bone; receiving, via the orientation sensor attached to the first bone, second information indicative of an orientation of the orientation sensor attached to the first bone; calculating, using the registered anatomic reference frame, the second information, and the rotational relationship, an orientation of the first bone relative to the anatomic reference frame; and calculating, using the orientation of the first bone relative to the anatomic reference frame, an anatomic alignment parameter between the first bone and at least one second bone.

Alternatively or additionally, the method can include measuring an angle of the at least one second bone in an anatomic plane of interest.

Alternatively or additionally, the method can include establishing a respective rotational relationship between respective reference frames of a respective orientation sensor attached to the at least one second bone and the at least one second bone; receiving, via each of the respective orientation sensors attached to the at least one second bone, third information indicative of a respective orientation of each of the respective orientation sensors attached to the at least one second bone; and calculating, using the registered anatomic reference frame, the third information, and the rotational relationship, a respective orientation of each of the at least one second bone relative to the anatomic reference frame. The anatomic alignment parameter between the first bone and the at least one second bone are calculated using the respective orientations of the first bone and the at least one second bone relative to the anatomic reference plane.

Alternatively or additionally, the method can include calculating, based on the registered anatomic reference frame, the second information into orientation relative to the anatomic reference frame.

Alternatively or additionally, registering the anatomic reference frame can include palpating one or more anatomic landmarks with a tool comprising the orientation sensor.

Alternatively or additionally, registering the anatomic reference frame can include performing kinematic registration with the orientation sensor attached to a patient's anatomy.

Alternatively or additionally, the method can include calibrating/zeroing the orientation sensor and the orientation sensor attached to the first bone to establish a common global reference frame.

Alternatively or additionally, establishing the rotational relationship between the respective reference frames of the orientation sensor attached to the first bone and the first bone can include using a mechanical instrument to align the orientation sensor in a known orientation relative to the first bone.

Alternatively or additionally, establishing the rotational relationship between the respective reference frames of the orientation sensor attached to the first bone and the first bone can include using an image of the first bone with the orientation sensor attached to the first bone.

Alternatively or additionally, establishing the rotational relationship between the respective reference frames of the orientation sensor attached to the first bone and the first bone can include deriving the rotational relationship based on respective rotational relationships between the respective reference frames of the orientation sensor attached to the first bone and the first bone relative to the anatomic reference frame.

Alternatively or additionally, the anatomic axis or plane is at least one of the sagittal, coronal, or transverse planes.

Alternatively or additionally, the anatomic axis or plane is a plane parallel to at least one of the sagittal, coronal, or transverse planes.

Alternatively or additionally, the anatomic axis or plane is parallel to at least one of longitudinal, transverse, or frontal axis.

Alternatively or additionally, the anatomic reference frame is specific to a certain portion of a patient's anatomy identified by bony landmarks.

Alternatively or additionally, the method can include displaying the anatomic alignment parameter between the first bone and the at least one second bone on a display device.

Alternatively or additionally, the anatomic alignment parameter is a joint angle or a spine alignment angle.

An example system for estimating anatomic alignment between two or more bones is also described herein. The system can include an elongated tool having first and second ends; a first orientation sensor coupled to the elongated tool; a second orientation sensor coupled to a first bone; a processor, communicatively coupled to the first and second orientation sensors. The processor can be configured to receive, via the first orientation sensor, first information indicative of an orientation of an anatomic axis or plane relative to a global reference frame; register, using the first information, an anatomic reference frame; establish a rotational relationship between respective reference frames of the second orientation sensor and the first bone; receive, via the second orientation sensor, second information indicative of an orientation of the second orientation sensor; calculate, using the registered anatomic reference frame, the second information, and the rotational relationship, an orientation of the first bone relative to the anatomic reference frame; and calculate, using the orientation of the first bone relative to the anatomic reference frame, an anatomic alignment parameter between the first bone and at least one second bone.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Figure 1:
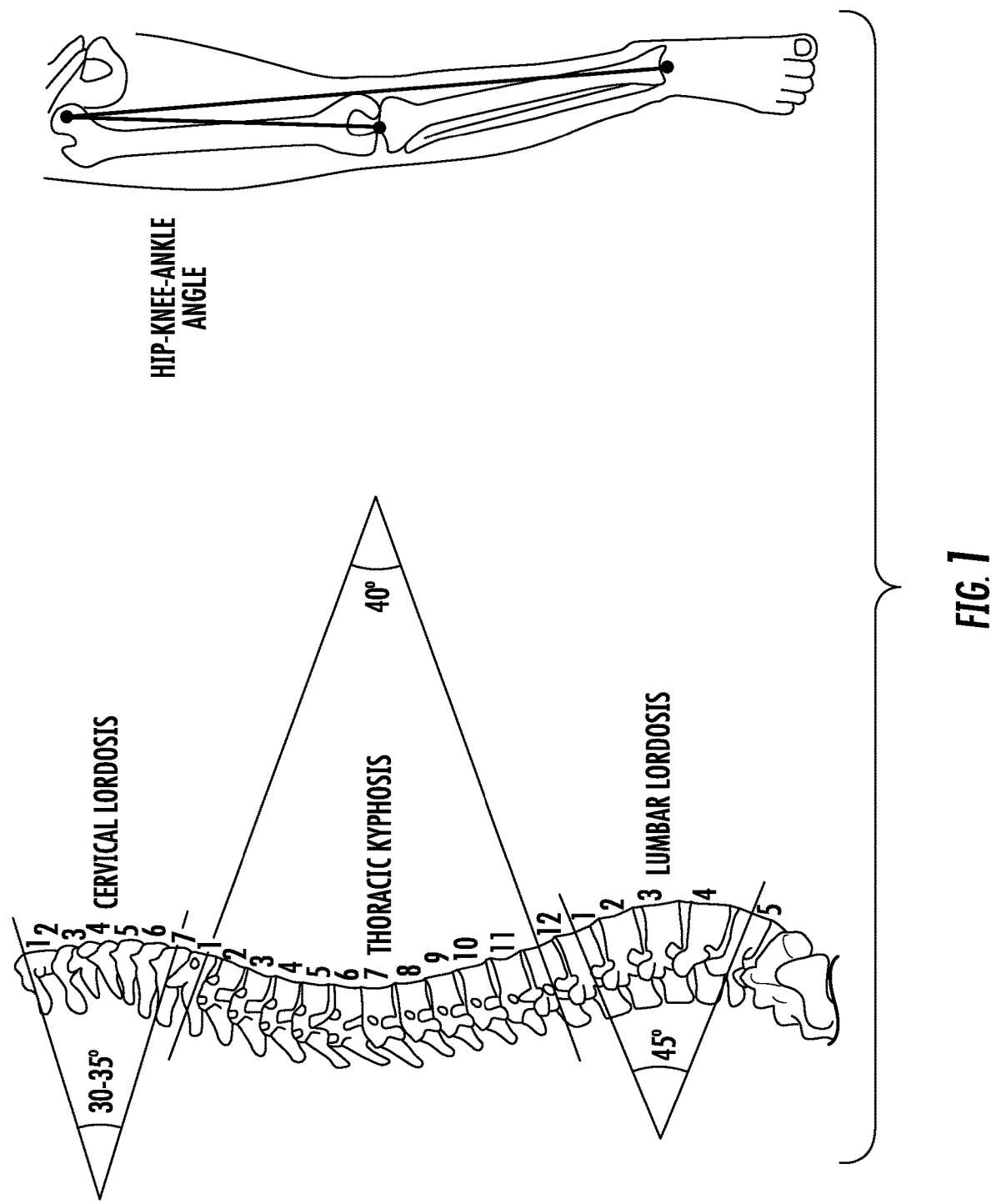
FIG. 1 illustrates example anatomic alignment parameters that can be measured according to implementations described herein.

FIG. 1 illustrates examples of anatomic alignment parameters that can be measured using methods and systems disclosed herein. As used herein, "anatomic alignment" or "alignment" refers to relative orientation between bones (e.g., two or more bones). Anatomic alignment parameters include, but are not limited to, spinal alignment angles and joint angles. Examples of such anatomic alignment parameters include spine alignment angles such as Cobb angles that can be measured in the sagittal and coronal planes. Example Cobb angles include, but are not limited to, Lumbar Lordosis and Thoracic Kyphosis, which are measured in the sagittal plane between specific vertebrae per surgeon preferences. In FIG. 1, Lumbar Lordosis is measured between vertebral segments S1 and L1 and Thoracic Kyphosis is measured between vertebral segments T12 and T1. It should be understood that the spine alignment angles (Lumbar Lordosis and Thoracic Kyphosis) shown in FIG. 1 and/or the vertebrae used for measurement of the same are provided only as examples. Another example anatomic alignment parameter is the Hip-Knee-Ankle angle, which is measured in the coronal plane between the femur and tibia as shown in FIG. 1. It should be understood that joint angle (Hip-Knee-Angle) shown in FIG. 1 and/or the locations used for measurement of the same are provided only as examples. This disclosure contemplates that the systems and methods described herein can be used to measure anatomic alignment parameters between bones other than those shown in FIG. 1. It is also contemplated that based on the measured alignment parameters and knowledge of the biomechanics of the anatomy or joint involved, positional relationships may also be estimated.

Figure 2:
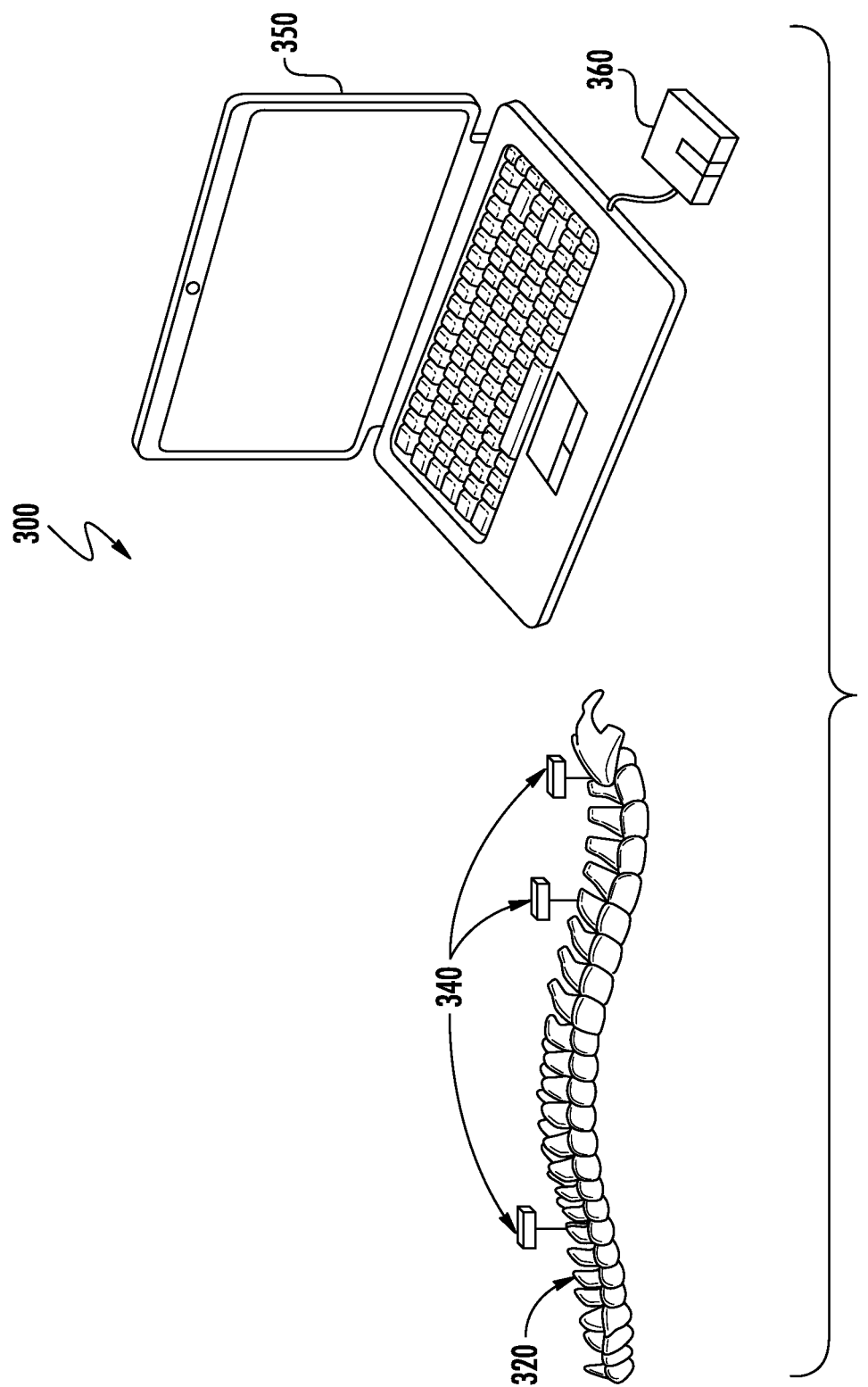
FIG. 2 is a diagrammatic view of an example vertebrae orientation measurement system used to measure anatomic alignment according to implementations described herein.

FIG. 2 illustrates an example anatomic orientation measurement system that can be used to measure the alignment between two or more vertebrae that comprise a patient's spine. In FIG. 2, the anatomic orientation measurement system is a spine surgical system. It should be understood that spinal surgery is only one example application in which the anatomic orientation measurement systems described herein can be used. As illustrated in FIG. 2, the surgical system 300 provides a solution for registering one or more anatomic reference planes, establishing the rotational relationship between one or more vertebrae relative to the respective orientation sensors coupled to the one or more vertebrae, measuring orientation relative to one or more anatomic planes or axes of one of more bones coupled to an orientation sensor, calculating alignment between two or more vertebrae in one or more anatomic planes, and displaying this information in real-time. It should be understood that the spine is only provided as an example of the patient's anatomy and that the systems and methods described herein are applicable to anatomy other than the spine and to bones other than the vertebra. For example, those skilled in the art will recognize that embodiments consistent with the presently disclosed systems and methods may be employed in any environment involving orthopedic procedures, such as the knee, hip, and shoulder.

For example, in accordance with the exemplary embodiment illustrated in FIG. 2, system 300 may embody a system for intra-operatively—and in real-time or near real-time—monitoring vertebral alignment in one or more anatomic reference planes. Individual components of exemplary embodiments of orthopedic placement monitoring system 300 will now be described in more detail.

As illustrated in FIG. 2, the system 300 comprises one or more orientation sensors 340 coupled to a processing and display unit 350. In some implementations, wireless communication is achieved via wireless communication transceiver 360, which may be operatively connected to processing and display unit 350. Any number orientation sensors can be placed on the anatomy depending on the application and number of anatomical segments to be independently tracked, desired resolution/accuracy of the alignment measurement, and type of information desired. For example, in FIG. 2, one orientation sensor may be placed on S1 vertebra of the spine 320, another one on vertebra L5, and another one on vertebra T1. Other or additional locations may be selected by the surgeon to achieve specific goals of the surgery. The system described herein facilitates the ability to miniaturize orientation sensor 340 such that they can be attached to small anatomical segments such as individual vertebrae. The orientation sensors 340 are placed on the anatomy using orthopedic screws, pins, or clamps commonly used in such procedures. Alternatively, the orientation sensors 340 may be attached using custom pins, screws, clamps or quick connect/disconnect mechanisms or any means that ensures rigid fixation to the anatomy. The orientation sensors 340 can be placed on any suitable anatomical feature that allows for rigid fixation such as the spinous or transverse processes. Attachment can be performed using any suitable percutaneous or open surgical technique. Note that although there is no technical limitation on the number of orientation sensors that can be used, a practical limit is expected to be around 20 orientation sensors. However, the quantity of orientation sensors used does not interfere with or limit the disclosure in any way.

As illustrated in FIG. 2, system 300 may include at least one orientation sensor 340 for estimating alignment of a bone (e.g. vertebra) relative to another bone (e.g. another vertebra) and a processing device (such as processing and display unit 350 or other computer device for processing and displaying data received by system 300), and one or more wireless communication transceivers 360 for communicating with one or more orientation sensors 340 attached to the patient's anatomy. The components of system 300 described above are exemplary only, and are not intended to be limiting. Indeed, it is contemplated that additional and/or different components may be included as part of system 300 without departing from the scope of the present disclosure. For example, although wireless communication transceiver 360 is illustrated as being a standalone device, it may be integrated within one or more other components, such as processing and display unit 350. Thus, the configuration and arrangement of components of system 300 illustrated in FIG. 2 are intended to be exemplary only.

Processing and display unit 350 (sometimes referred to herein as "processing system 350") may include or embody any suitable microprocessor-based device configured to process and/or analyze information indicative of anatomic alignment. According to one implementation, processing system 350 may be a general purpose computer programmed with software for receiving, processing, and displaying information indicative of anatomic orientation. According to other implementations, processing system 350 may be a special-purpose computer, specifically designed to communicate with, and process information for, other components associated with system 300. Individual components of, and processes/methods performed by, processing and display unit 350 will be discussed in more detail below.

Processing and display unit 350 may be communicatively coupled to one or more orientation sensors 340 and may be configured to receive, process, and/or analyze data measured by the orientation sensors 340. According to one implementation, processing system 350 may be wirelessly coupled to orientation sensor 340 via wireless communication transceiver(s) 360 operating any suitable protocol for supporting wireless (e.g., wireless USB, ZigBee, Bluetooth, Wi-Fi, etc.) In accordance with another implementation, processing and display unit 350 may be wirelessly coupled to orientation sensor 340, which, in turn, may be configured to collect data from the other constituent sensors and deliver it to processing system 350. In accordance with yet another implementation, certain components of processing and display unit 350 (e.g. I/O devices 356 as shown in FIG. 3) may be suitably miniaturized for integration with sensor 340.

Wireless communication transceiver(s) 360 may include any device suitable for supporting wireless communication between one or more components of system 300. As explained above, wireless communication transceiver(s) 360 may be configured for operation according to any number of suitable protocols for supporting wireless, such as, for example, wireless USB, ZigBee, Bluetooth, Wi-Fi, or any other suitable wireless communication protocol or standard. According to one implementation, wireless communication transceiver 360 may embody a standalone communication module, separate from processing and display unit 350. As such, wireless communication transceiver 360 may be electrically coupled to processing and display unit 350 via USB or other data communication link and configured to deliver data received therein to processing and display unit 350 for further processing/analysis. According to other implementation, wireless communication transceiver 360 may embody an integrated wireless transceiver chipset, such as the Bluetooth, Wi-Fi, NFC, or 802.11x wireless chipset included as part of processing and display unit 350.

Figure 3:
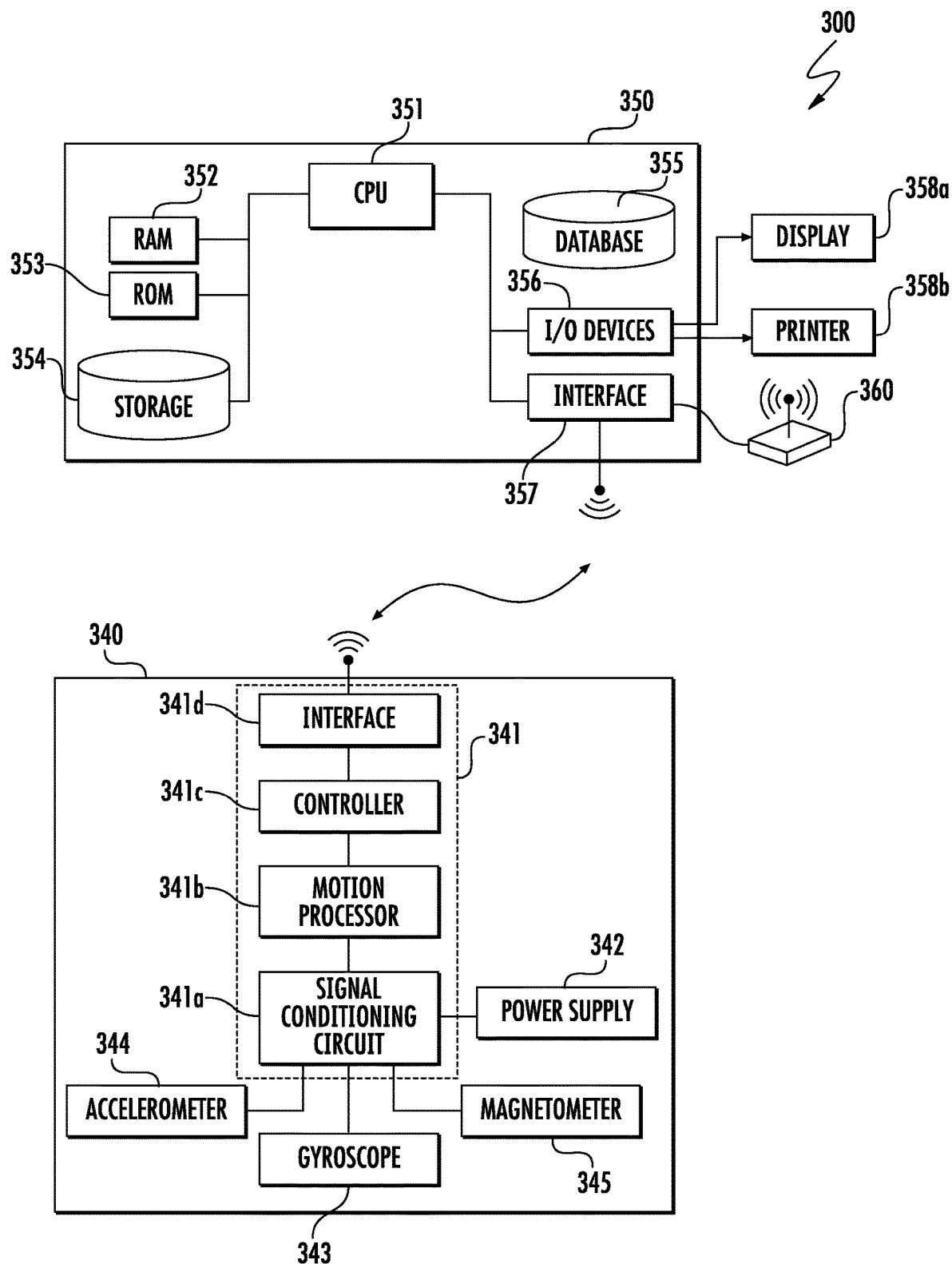
FIG. 3 is a schematic view of example components associated with an anatomic orientation measurement system, such as the vertebrae orientation measurement system illustrated in FIG. 2.

FIG. 3 provides a schematic diagram illustrating certain exemplary subsystems associated with system 300 and its constituent components. Specifically, FIG. 3 is a schematic block diagram depicting exemplary subcomponents of processing and display unit 350 and orientation sensor 340 in accordance with certain disclosed embodiments.

As explained, processing and display unit 350, also herein referred to as processing system, may be any processor-based computing system that is configured to receive and process alignment information associated with anatomy (e.g., anatomy 320 shown in FIG. 2 such as one or more bones of a spine), receive and store anatomic registration information, receive and store information indicative of rotational relationship between one or more orientation sensors and respective bones coupled to them, analyze the received orientation data indicative of orientation of one or more bones relative to one or more anatomic planes or axes, and calculate the alignment between two or more bones of a spine in one more of patient's anatomic reference planes, and output the extracted data in real-time or near real-time. Non-limiting examples of processing and display unit 350 include a desktop or notebook computer, a tablet device, a smartphone, wearable computers including augmented-/virtual reality glasses or headsets, handheld computers, or any other suitable processor-based computing system. Alternatively, the display 358a could be separate from the processing system 350 and could be any suitable display such as a monitor, projector, and/or wearable head mounted displays or augmented reality glasses that overlay virtual information on a view of the real world.

For example, as illustrated in FIG. 3, processing system 350 may include one or more hardware and/or software components configured to execute software programs, such as alignment of vertebrae of spine (e.g., spine 320 shown in FIG. 2) and displaying information. According to one implementation, processing system 350 may include one or more hardware components such as, for example, a central processing unit (CPU) or microprocessor 351, a random access memory (RAM) module 352, a read-only memory (ROM) module 353, a memory or data storage module 354, a database 355, one or more input/output (I/O) devices 356, and an interface 357. Alternatively and/or additionally, processing system 350 may include one or more software media components such as, for example, a computer-readable medium including computer-executable instructions for performing methods consistent with certain disclosed embodiments. It is contemplated that one or more of the hardware components listed above may be implemented using software. For example, storage 354 may include a software partition associated with one or more other hardware components of processing system 350. Processing system 350 may include additional, fewer, and/or different components than those listed above. It is understood that the components listed above are exemplary only and not intended to be limiting.

CPU 351 may include one or more processors, each configured to execute instructions and process data to perform one or more functions associated with processing system 350. As illustrated in FIG. 3, CPU 351 may be communicatively coupled to RAM 352, ROM 353, storage 354, database 355, I/O devices 356, and interface 357. CPU 351 may be configured to execute sequences of computer program instructions to perform various processes, which will be described in detail below. The computer program instructions may be loaded into RAM 352 for execution by CPU 351.

RAM 352 and ROM 353 may each include one or more devices for storing information associated with an operation of processing system 350 and/or CPU 351. For example, ROM 353 may include a memory device configured to access and store information associated with processing system 350, including information for identifying, initializing, and monitoring the operation of one or more components and subsystems of processing system 350. RAM 352 may include a memory device for storing data associated with one or more operations of CPU 351. For example, ROM 353 may load instructions into RAM 352 for execution by CPU 351.

Storage 354 may include any type of mass storage device configured to store information that CPU 351 may need to perform processes consistent with the disclosed embodiments. For example, storage 354 may include one or more magnetic and/or optical disk devices, such as hard drives, CD-ROMs, DVD-ROMs, or any other type of mass media device. Alternatively or additionally, storage 354 may include flash memory mass media storage or other semiconductor-based storage medium.

Database 355 may include one or more software and/or hardware components that cooperate to store, organize, sort, filter, and/or arrange data used by processing system 350 and/or CPU 351. For example, database 355 may include historical data such as, for example, stored orientation data associated with the anatomy as well imaging data for registration. CPU 351 may access the information stored in database 355 to provide a comparison between previous alignment data (or planned alignment data) and current alignment (i.e., real-time) data. CPU 351 may also analyze current and previous placement parameters to identify trends in historical data. These trends may then be recorded and analyzed to allow the surgeon or other medical professional to compare the orientation data with different prosthesis designs and patient demographics. It is contemplated that database 355 may store additional and/or different information than that listed above. It is also contemplated that database 355 may also be replicated on a remote server on the "cloud" and accessed via wide and/or local area networks.

I/O devices 356 may include one or more components configured to communicate information with a user associated with system 300. For example, I/O devices may include a console with an integrated keyboard and mouse to allow a user to input parameters associated with processing system 350. Alternatively, I/O device 356 may be a touch screen. I/O devices 356 may also include a display including a graphical user interface (GUI) for outputting information on a display monitor 358a. I/O devices 356 may also include peripheral devices such as, for example, a printer 358b for printing information associated with processing system 350, a user-accessible disk drive (e.g., a USB port, a floppy, CD-ROM, or DVD-ROM drive, etc.) to allow a user to input data stored on a portable media device, a microphone, a speaker system, a gesture recognition system, or any other suitable type of interface device that allows for tactile, voice, gesture, or other human input.

Interface 357 may include one or more components configured to transmit and receive data via a communication network, such as the Internet, a local area network, a workstation peer-to-peer network, a direct link network, a wireless network, or any other suitable communication platform. For example, interface 357 may include one or more modulators, demodulators, multiplexers, demultiplexers, network communication devices, wireless devices, antennas, modems, and any other type of device configured to enable data communication via a communication network. According to one implementation, interface 357 may be coupled to or include wireless communication devices, such as a module or modules configured to transmit information wirelessly using Wi-Fi or Bluetooth wireless protocols. Alternatively or additionally, interface 357 may be configured for coupling to one or more peripheral communication devices, such as wireless communication transceiver 360. In certain implementations, interface 357 may be coupled to intraoperative imaging devices just as C-arms to receive images for processing and/or registration. Interface 357 may also similarly coupled to hospital/clinical Picture Archiving and Communication Systems (PACS).

As explained, orientation sensor 340 may include one or more subcomponents configured to detect and transmit information that either represents 3-dimensional (3D) orientation (e.g. pitch, yaw, and roll) with respect to a 3-dimensional reference frame. The 3-dimensional reference frame may be a global reference frame as defined by the North-East-Down (NED) convention utilized in inertial navigation or any other absolute frame defined globally or locally. It should be understood that a global frame may have meaning beyond the local environment of the surgery, while a local frame is defined in the environment local to the surgery. As used herein, the term "global frame" refers to any absolute refence frame that is independent of the anatomy and sensor whether defined globally or locally. According to one implementation, orientation sensor(s) 340 may be an inertial measurement unit including a microprocessor 341, a power supply 342, and one or more of a gyroscope 343, an accelerometer 344, or a magnetometer 345.

According to one implementation, inertial measurement unit(s) 340 may contain a 3-axis gyroscope 343, a 3-axis accelerometer 344, and a 3-axes magnetometer 345. It is contemplated, however, that fewer of these devices with fewer axes can be used without departing from the scope of the present disclosure. For example, according to one implementation, inertial measurement units may include only a gyroscope and an accelerometer, the gyroscope for calculating the orientation based on the rate of rotation of the device, and the accelerometer for measuring earth's gravity and linear acceleration, the accelerometer providing corrections to the rate of rotation information (based on errors introduced into the gyroscope because of device movements that are not rotational or errors due to biases and drifts). In other words, the accelerometer may be used to correct the orientation information collecting by the gyroscope. Similar the magnetometer 345 can be utilized to measure the earth's magnetic field and can be utilized to further correct gyroscope errors. Thus, while all three of gyroscope 343, accelerometer 344, and magnetometer 345 may be used, orientation measurements may be obtained using as few as one of these devices. The use of additional devices increases the resolution and accuracy of the orientation information and, therefore, may be advantageous when orientation accuracy is important.

As illustrated in FIG. 3, microprocessor 341 of inertial measurement unit 340 may include different processing modules or cores, which may cooperate to perform various processing functions. For example, microprocessor 341 may include, among other things, an interface 341d, a controller 341c, a motion processor 341b, and signal conditioning circuitry 341a. Controller 341c may be configured to control and receive conditioned and processed data from one or more of gyroscope 343, accelerometer 344, and magnetometer 345 and transmit the received data to one or more remote receivers. The data may be pre-conditioned via signal conditioning circuitry 341a, which includes amplifiers and analog-to-digital converters or any such circuits. The signals may be further processed by a motion processor 341b. Motion processor 341b may be programmed with so-called "motion fusion" algorithms to collect and process data from different sensors to generate error corrected orientation information. Such motion fusion algorithms may be 6 degree of freedom (6DOF) algorithms utilizing information from 3-axis accelerometers and 3-axis gyroscopes or 9 degree of freedom algorithms utilizing information from 3-axis magnetometers in addition to the 3-axis accelerometers and gyroscopes. However both algorithms are capable of estimating 3 dimensional orientation and suitable for use in the methods and systems described herein. The orientation information may be a mathematically represented as an orientation or rotation quaternion, euler angles, direction cosine matrix, rotation matrix of any such mathematical construct for representing orientation known in the art. Accordingly, controller 341c may be communicatively coupled (e.g., wirelessly via interface 341d as shown in FIG. 3, or using a wireline protocol) to, for example, processing system 350 and may be configured to transmit the orientation data received from one or more of gyroscope 343, accelerometer 344, and magnetometer 345 to processing system 350, for further analysis.

Interface 341d may include one or more components configured to transmit and receive data via a communication network, such as the Internet, a local area network, a workstation peer-to-peer network, a direct link network, a wireless network, or any other suitable communication platform. For example, interface 341d may include one or more modulators, demodulators, multiplexers, demultiplexers, network communication devices, wireless devices, antennas, modems, and any other type of device configured to enable data communication via a communication network. According to one implementation, interface 341d may be coupled to or include wireless communication devices, such as a module or modules configured to transmit information wirelessly using Wi-Fi or Bluetooth wireless protocols. As illustrated in FIG. 2, inertial measurement unit(s) 340 may be powered by power supply 342, such as a battery, fuel cell, MEMs micro-generator, or any other suitable compact power supply.

Importantly, although microprocessor 341 of inertial measurement unit 340 is illustrated as containing a number of discrete modules, it is contemplated that such a configuration should not be construed as limiting. Indeed, microprocessor 341 may include additional, fewer, and/or different modules than those described above with respect to FIG. 3, without departing from the scope of the present disclosure. Furthermore, in other instances of the present disclosure that describe a microprocessor are contemplated as being capable of performing many of the same functions as microprocessor 341 of inertial measurement unit 340 (e.g., signal conditioning, wireless communications, etc.) even though such processes are not explicitly described with respect to microprocessor 341. Those skilled in the art will recognize that many microprocessors include additional functionality (e.g., digital signal processing functions, data encryption functions, etc.) that are not explicitly described here. Such lack of explicit disclosure should not be construed as limiting. To the contrary, it will be readily apparent to those skilled in the art that such functionality is inherent to processing functions of many modern microprocessors, including the ones described herein.

Microprocessor 341 may be configured to receive data from one or more of gyroscope 343, accelerometer 344, and magnetometer 345 and transmit the received data to one or more remote receivers. Accordingly, microprocessor 341 may be communicatively coupled (e.g., wirelessly (as shown in FIG. 3, or using a wireline protocol) to, for example, processing system 350 and configured to transmit the orientation data received from one or more of gyroscope 343, accelerometer 344, and magnetometer 345 to processing system 350, for further analysis. As illustrated in FIG. 3, microprocessor 341 may be powered by power supply 342, such as a battery, fuel cell, MEMs micro-generator, or any other suitable compact power supply.

Figure 4A:
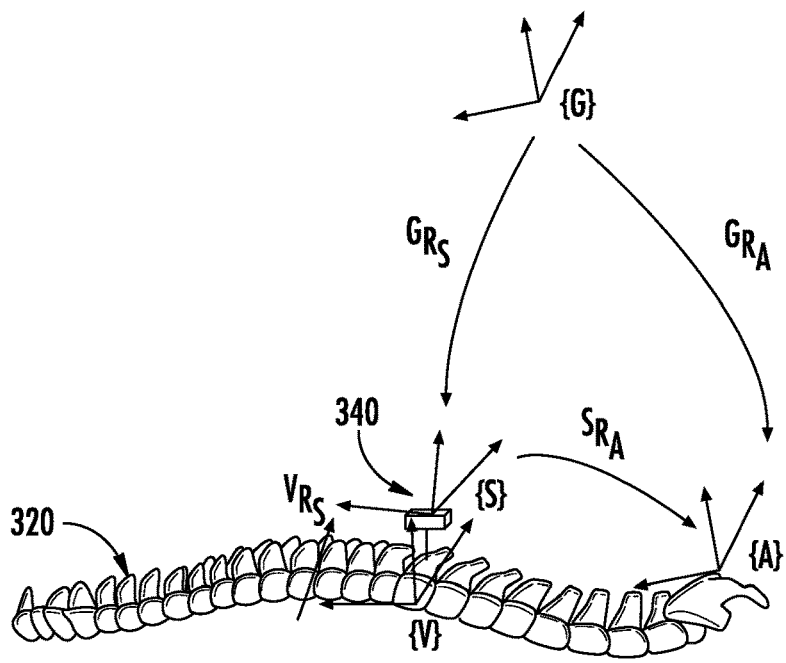
FIG. 4A is a diagrammatic view of the rotational relationships between various coordinate frames according to implementations described herein.

As explained, in order for system 300 to estimate anatomically correct alignment between two or more bones in one or more anatomic planes, the anatomic reference planes have to be registered. As used herein, a "reference plane" refers to any plane in a three dimensional (3D) Cartesian coordinate frame in Euclidean space. FIG. 4A illustrates the various coordinate frames involved in the calculation of the anatomic alignment consistent with certain embodiments disclosed herein. This disclosure contemplates that the operations described below with regard to FIG. 4A can be implemented using the system 300 shown in FIGS. 2 and 3. Each orientation sensor 340 has its own coordinate frame represented by {S} that is fixed to the sensor and moves with it. Each orientation sensor 340 measures the orientation of its respective frame {S} relative to a reference coordinate frame such as global reference frame {G}. As previously stated, {G} is any fixed absolute frame independent of the sensor or anatomy, e.g., it is fixed with respect to the environment shown in FIG. 4A. As described above, the global reference frame {G} can optionally be defined by the NED convention utilized in inertial navigation. It should be understood that frame {G} should not be limited to being defined by NED convention and can be any arbitrary fixed frame. For example, {G} can be orientation of the sensors on power up and can be recorded and stored as {G}. Orientation of the sensor frame {S} relative to {G} is represented by rotational transformation GRS, which is the fundamental information measured by the orientation sensor 340 prior to use in any application. Rotational transformation $^{G}R_{S}$ can be expressed in a variety of mathematical representations know in the art such as euler angles, direction cosine matrix, and quaternions.

When more than one orientation sensor 340 is used in the system (e.g., system 300 shown in Figs. and 3), each orientation sensor 340 may have a slightly different global reference frame. A process of calibration/zeroing can be utilized to harmonize the global reference frames of the orientation sensors 340 prior to using the orientation sensors 340. One skilled in the art will recognize that there are many ways to measure the differences between the respective global reference frames of a plurality of orientation sensors for the purposes of zeroing. One example method is to measure the respective orientations of the orientation sensors 340 when there is a known orientation relationship between them. For example, the orientation sensors 340 can be temporarily placed on an alignment (or zeroing) plate or jig that mechanically establishes a known orientation between them, preferably in alignment with zero relative rotation. When the orientation sensors 340 report their respective orientations in this arrangement, the relationship between the global reference frames can be established and the differences can be zeroed out. Alternatively or additionally, the plate or jig may be moved through known rotations or motions to collect zeroing data at different orientations to improve accuracy and precision of the zeroing. In effect, the zeroing process calibrates/zeroes the global reference frames of the orientation sensors into a common global reference frame. It should be understood that that when multiple sensors are used {G} represents this harmonized global reference.

Even after calibration/zeroing, the orientation $^{G}R_{S}$ measured by a plurality of orientation sensors 340 with respect to a reference frame (e.g., frame {G} in FIG. 4A) is not very meaningful from an anatomic perspective. Therefore, a method of registration is utilized to establish the orientation $^{G}R_{A}$ between the reference frame {G} and the anatomic reference frame {A}. Example registration techniques that can be used to establish relationship $^{G}R_{A}$ are described in detail below with regard to FIGS. 5A and 5B. Once the relationship $^{G}R_{A}$ is established, the orientation of the orientation sensors 340 in the anatomic reference frame, which is represented by $^{S}R_{A}$, can be calculated. For example, if the rotations are unit quaternions, the following formula can be used:

$$^{S}R_{A} = (^{G}R_{S})^{-1} * {^{G}R_{A}}$$

This can be done for any number of orientation sensors. Thereafter, alignment or relative orientation between the orientation sensors 340 can then be calculated in the anatomic reference frame of interest as described below. For example if $a_{si}$ is orientation of sensor "i" in the anatomic reference plane and $a_{sj}$ is orientation of sensor "j" in the same plane, then $a_{sj} - a_{si}$ is the relative orientation or alignment between the sensors in the anatomic reference plane.

Figure 4B:
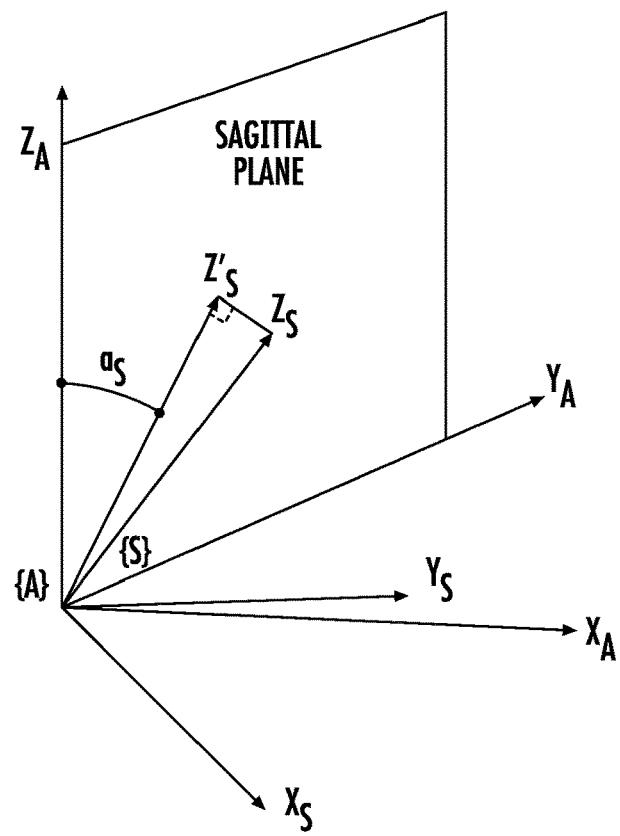
FIG. 4B is a graphical view of the orientation sensor measurement in the anatomic reference plane of the anatomic coordinate frame.

Referring to FIG. 4B, an example calculation of orientation of orientation sensor 340 in a reference anatomic plane is shown graphically. This disclosure contemplates that the operations described below with regard to FIG. 4B can be implemented using the system 300 shown in FIGS. 2 and 3. Frame {S}, which is the coordinate frame of an orientation sensor 340, is represented by reference axes $X_S$, $Y_S$, $Z_S$, and frame {A}, which is the anatomic reference frame, is represented by reference axes $X_A$, $Y_A$, $Z_A$. The orientation of sensor frame {S} is shown in the anatomic frame {A} after registration of the anatomic frame as described above. The anatomic reference plane in this example is the sagittal plane or the $Z_A Y_A$ plane as shown in FIG. 4B. It should be understood that the anatomic reference plane is not limited to the sagittal plane. This disclosure contemplates that the anatomic reference plane can be, but is not limited to, the coronal plane, sagittal plane, or transverse plane of the patient's body. It should be understood that the anatomic reference plane is not limited to the three principal anatomic planes provided as examples. One example method to calculate to the orientation of the orientation sensor 340 in the anatomic reference plane (sagittal plane in FIG. 4B) is to calculate the projection of a reference axis in the sensor frame {S} (in this example $Z_S$) on the anatomic reference plane, shown as $Z_S'$. One example method to calculate this is to zero the component of the vector orthogonal to the plane of interest. The angle as of $Z_S'$ in the anatomic reference plane can then be calculated for this and any other sensor. In case of a plurality of orientation sensors 340, relative angles or alignment can be calculated in the anatomic plane.

In some implementations, and referring again to FIG. 4A, the relationship $^V R_S$ between the sensor frame {S} and the frame of reference of the bone {V} (e.g., a vertebra) to which the orientation sensor 340 is attached may also need to be established. For example, as show FIG. 4A, the orientation sensor 340 is attached to a vertebra, where the vertebra can be at an arbitrary orientation with respect to the orientation sensor 340 such that the orientation of the orientation sensor 340 or the registered anatomy does not represent the true orientation of the vertebra. Example techniques that can be used to establish relationship $^V R_S$ are described in detail below with regard to FIGS. 6A and 6B.

Figure 5A:
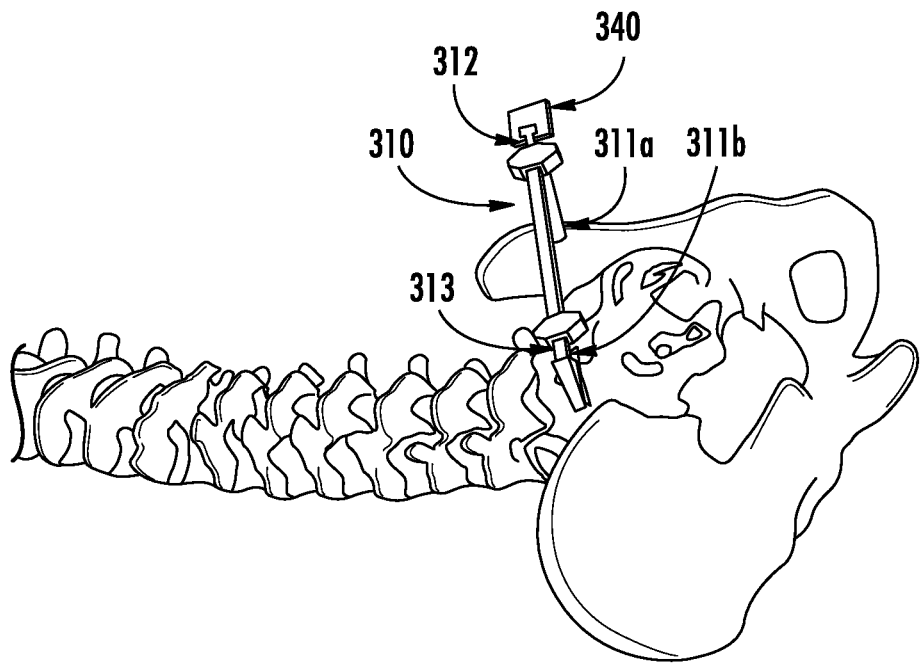
FIG. 5A illustrates an example position of a tool during a registration process that involves estimating an orientation of a first reference anatomic plane according to implementations described herein.
Figure 5B:
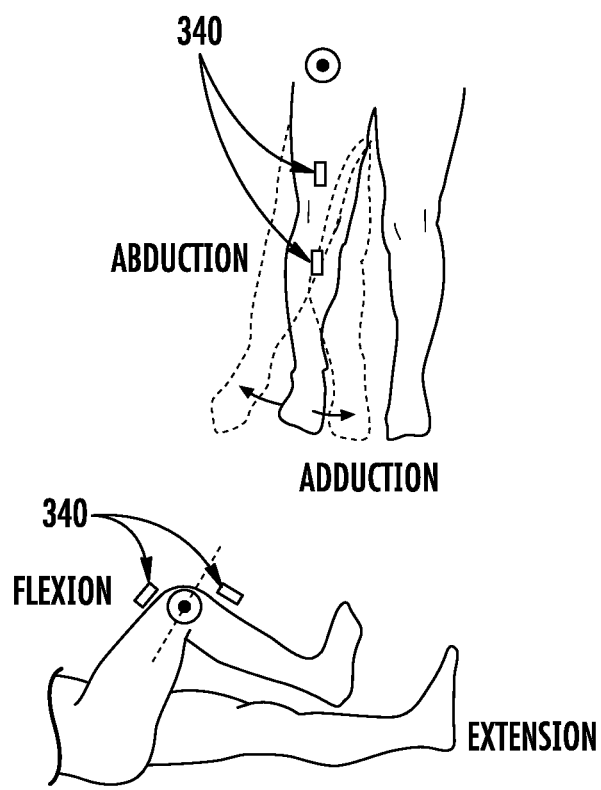
FIG. 5B illustrates an example method for kinematically registering one or more anatomic planes according to implementations described herein.

FIGS. 5A and 5B illustrate example methods for registration of anatomic reference frames. FIG. 5A illustrates a method using anatomic landmarks. As illustrated in FIG. 5A, this method includes use of tool 310 with an elongated member having a longitudinal axis that extends between a first end 312 and a second end 313. Pointers 311a, 311b are any structure(s) suitable for interfacing with a portion of a patient's anatomy to provide a uniform offset of tool 310 to the portion of the patient's anatomy. According to one implementation, pointers 311a, 311b are sized and designed such that when they are placed on a flat surface, the longitudinal axis of tool 310 is maintained parallel to the flat surface. As such, pointers 311a, 311b offset the longitudinal axis of the tool equally from the portions of the patient's anatomy that they are in contact with. According to one implementation, at least one of the pointers is designed with a sliding mechanism so that the lateral distance between pointers 311a, 311b can be varied by sliding the pointer along the shaft of tool 310.

A common anatomic reference plane utilized is the sagittal plane which can be calculated from the locations of the left and right posterior superior iliac spines (PSIS) with the patient in prone or lateral position. It should be understood that the left and right anterior iliac spines (ASIS) can be utilized if the patient is supine. Additionally, the anatomic reference plane is not limited to the sagittal plane and can alternatively be the coronal plane, transverse plane, or any other anatomic plane. As illustrated in FIG. 5A, pointers 311a, 311b of tool 310 are placed at portions of the patient's anatomy that correspond to the left and right PSIS of the pelvis. In this position, the orientation sensor 340 measures the orientation associated with tool 310 which corresponds to the orientation of an anatomic axis that passes through the patient's left and right PSIS's. During a surgical procedure, pointers 311a, 311b are brought in contact with a patient's anatomy corresponding to estimated positions of the two PSIS landmarks. When the user is satisfied with the position of pointers 311a, 311b, the orientation associated with tool 310 is measured by the orientation sensor 340 and transmitted to a processing system (e.g., processing and display unit 350 shown in FIGS. 2 and 3) for storage. One or more positions may be be recorded and averaged to improve accuracy. Using mathematical formulas based on geometry, the processing system can calculate the orientation of a plane that is perpendicular to this recorded orientation (e.g., the anatomic axis passing through the left and right PSIS's), which is representative of the sagittal plane.

The process can be repeated to register additional planes and axes in one or more anatomic reference planes using additional landmarks. For example, the spinous process of a vertebra such as C7 may be utilized as an additional landmark, and an axis passing through one of the PSIS and C7 recorded with orientation sensor 340 on tool 310 (with suitable length extension to allow palpation of both landmarks). This axis can then be utilized along with the axis between the two PSIS to calculate the orientation of a second anatomic plane such as the coronal plane. Similarly, any of number of reference points/planes or combinations thereof that can be used to define one or more reference anatomic coordinate frames without departing from the scope of the present disclosure. For example, the orientation of the axial or transverse plane that is orthogonal to both the coronal and sagittal plane can be calculated.

FIG. 5B illustrates an alternate method for registering anatomic reference frames. In this method, instead of anatomic landmarks, anatomic motions are utilized. Such methods can therefore be referred to as "kinematic". In kinematic registration, one or more orientation sensors 340 are mounted onto portion of the anatomy that are then moved in one or more anatomic planes or around one or more axes or around one or more points. For example, as shown in FIG. 5B, orientation sensors 340 are placed on the upper and lower legs of the patient. The leg is then moved in abduction-adduction and/or flexion-extension which occur in planes parallel to the coronal and sagittal planes, respectively. Similarly as described above, the orientation sensors 340 can transmit the axis of rotation and/or plane of rotation for each motion to a processing system (e.g., processing and display unit 350 shown in FIGS. 2 and 3) for storage. The sagittal and coronal anatomic reference planes or axes can then be derived from this information. Additionally, the orientation of the axial or transverse plane that is orthogonal to both the coronal and sagittal plane can be calculated.

Figure 6A:
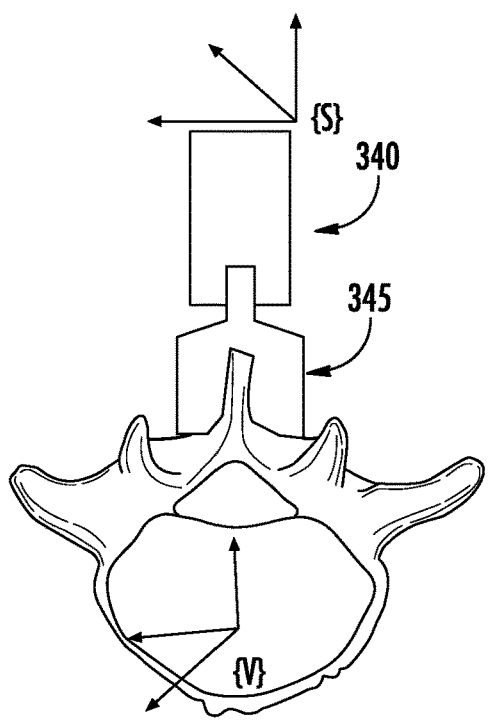
FIG. 6A illustrates an example method of establishing the rotational relationship between a bone (vertebra) and an orientation sensor coupled to the bone according to implementations described herein.

Referring to FIG. 6A, as discussed above with regard to FIG. 4A, in certain implementations the rotational relationship $^V R_S$ between the sensor frame {S} and the frame of reference of the bone represented by its reference planes and/or axes {V} (e.g., vertebra) to which an orientation sensor 340 is attached to may also need to be established. This is especially the case when the orientation sensor 340 is attached at an arbitrary user defined orientation with respect to the bone (e.g., vertebra). One method to establish this relationship $^V R_S$ is mechanically via alignment jigs or other instrumentation that either attaches the orientation sensor 340 in alignment to the bone (in this case $^V R_S$ represents a zero rotation), or in a known fixed orientation with respect to the bone, or alternatively an instrument like a goniometer measures the rotational relationship between them. An example of mechanical instrumentation that can be used to attach the sensor to the bone are patient specific instruments/guides 345 as shown in FIG. 6A. Patient-specific instruments typically utilize pre-operative 3D imaging of the patient's anatomy. These instruments typically have matching/interlocking features that are representative of the inverse of the patient's anatomic features and/or other such patient specific features such as the spinous process and surrounding area as shown in FIG. 6A. These features allow fixation of the patient-specific instrumentation onto the patient's bone during surgery such that a pre-determined orientation of the instruments relative to the patient's anatomy is established. In one implementation as shown in FIG. 6A, orientation sensor 340 is embedded into or attached to a patient-specific instrument 345 such that the orientation of the orientation sensor 340 with respect to the patient-specific instrument 345 is known. Alternatively, the orientation sensor 340 can be attached to the patient-specific instrument intra-operatively at a known orientation using mating features on the patient-specific instrument 345 or alignment marks. Also, as previously mentioned, the patient-specific instrument is designed for fixation to the patient's anatomy at a pre-determined anatomic orientation with respect to reference anatomic reference planes or axes of the bone. With the above two pieces of information—specifically 1) the orientation of sensor 340 relative to patient-specific instrument 345 and 2) orientation of patient-specific instrument 345 relative to anatomic reference planes or axes of the bone—the relative orientation of the orientation sensor 340 with respect to any anatomic plane, landmark, or axis of the bone, represented by $^{V}R_{S}$ can be calculated. An alternate method to the mechanical method is to use a camera to image the orientation sensor 340 and visible vertebrae and using image processing algorithms and or manual methods to establish the relationship. Cameras that give depth information such as stereo or time-of-flight are well suited for this task. In minimally invasive surgeries where the vertebrae is not exposed, intra operative X-ray based two dimensional (2D) or 3D imaging may be utilized for a one time registration.

An alternate method for calculating rotation $^{V}R_{S}$ is to do it indirectly by establishing the orientation of vertebra and the orientation sensor 340 in the anatomic reference frame {A} and calculating the relative orientation in that frame. This is can be done in 2 or 3 dimensions depending on the application. Several methods exist for establishing the orientation of vertebra in anatomic frame {A}. In one method, the bone with the orientation sensor 340 attached is manually held in alignment to frame {A} or in a known orientation with respect to frame {A}. This gives the orientation of bone frame {V} relative to the anatomic frame {A}. Concurrently, the orientation of the orientation sensor 340 frame {S} in the anatomic frame {A} in that position is recorded. With the above two pieces of information, relative orientation of {V} with respect to {S} in the anatomic frame {A} can be calculated.

Figure 6B:
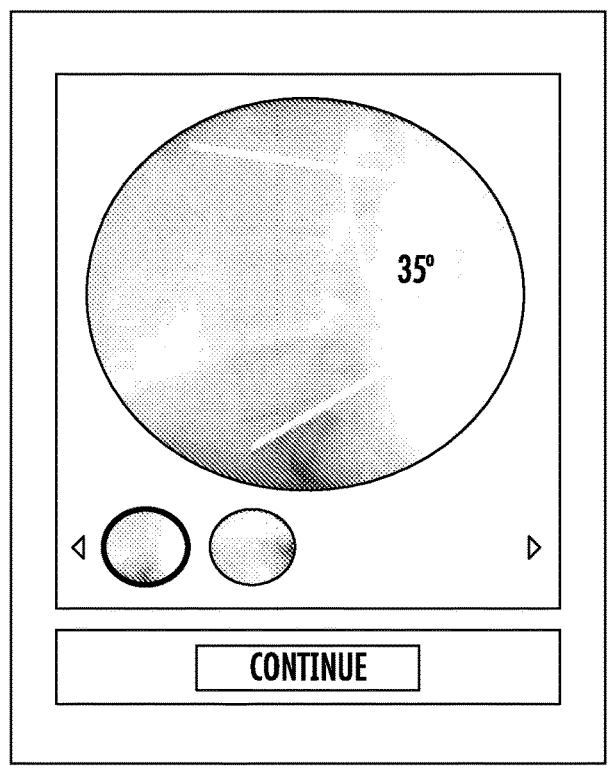
FIG. 6B illustrates an example method of establishing the rotational relationship between bone (vertebra) and an orientation sensor coupled to the bone.

An alternate method for establishing this relationship is shown in FIG. 6B. This method relies on an intra-operative image such as an X-ray or fluoroscope image taken with the image plane of the imaging device parallel to an anatomic plane of {A}. The orientation of a reference axis or plane of the vertebrae (such as a line drawn parallel to a vertebral end plate) can then be measured. Concurrently, the orientation of orientation sensor 340 attached to bone at the time of imaging can measured in the same anatomic plane, using the method described previously with reference to FIG. 4B. The relative orientation of vertebrae with respect to the sensor in the anatomic plane can then be calculated. The process may be repeated for additional planes such as coronal and axial/transverse planes depending on the application.

Once the relationship $^{V}R_{S}$ is established as needed using the methods described above, the angle $a_{s}$ of the orientation sensor 340 in the anatomic frame {A} as calculated in FIG. 4B can be converted into an angle $a_{v}$ representing the angle of the bone in the anatomic reference plane. The angle $a_{v}$ for two or more bones can then be used to calculate the alignment between the bones. For example, if $a_{vi}$ is orientation of bone "i" in the anatomic reference plane and $a_{vj}$ is orientation of bone "j" in the same plane, then $a_{vj}-a_{vi}$ is the relative orientation or alignment between the bones in the anatomic reference plane. In some implementations, a bone may not be tracked by an orientation sensor 340 if such bone is not expected to move during the surgery (e.g., the pelvis in some surgeries). In these implementations, the angle $a_{v}$ is the angle of the bone measured in the anatomic plane of interest and can, for example, be a one-time measurement during registration without the need to couple an orientation sensor to such bone and determine $^{V}R_{S}$. In other implementations, respective orientation sensors 340 are attached to each of at least two bones, and $^{V}R_{S}$ is calculated for each bone as described herein.

Figure 7:
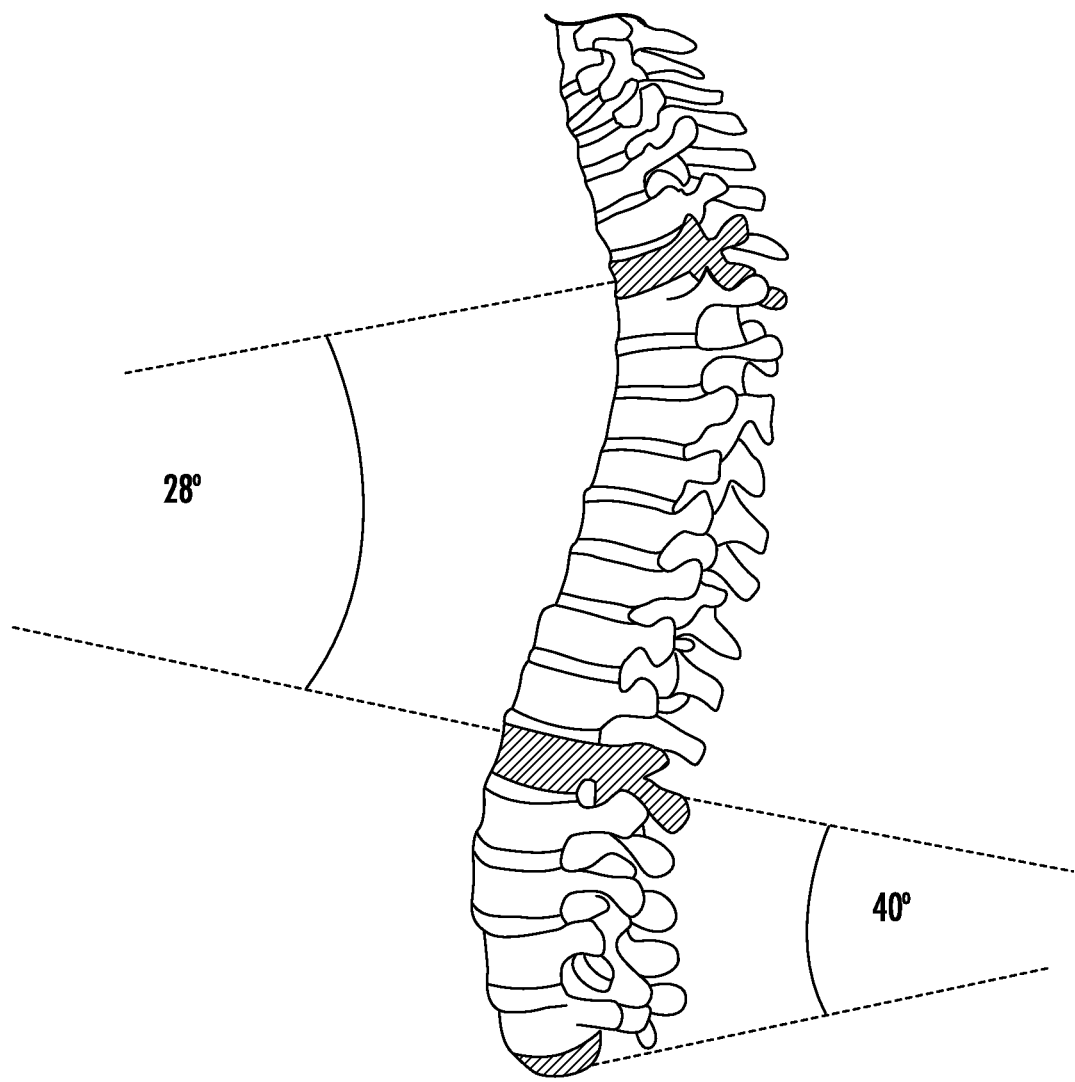
FIG. 7 illustrates an example display that may be provided on a monitor or output device for intra-operatively displaying the measured anatomic alignment parameters in real time according to implementations described herein.

FIG. 7 provides an example screen shot corresponding to a graphical user interface (GUI) associated with processing and display unit such as processing and display unit 350 shown in FIGS. 2 and 3. As illustrated in screen shot, GUI may include a user interface that is configured to display, in real-time or near-real time, the alignment between two or more vertebrae relative in one or more reference anatomic planes. According to one implementation, user interface element may provide a first numerical gauge that displays the angle of vertebra L5 relative to vertebra S1 (e.g., 40° in FIG. 7) and a second numerical gauge that displays the angle of vertebra T4 relative to vertebra L5 (e.g., 28° in FIG. 7). These angle are referred to as Lordosis and Kyphosis, respectively. It should be understood that the specific vertebrae used for the alignment measurements shown in FIG. 7 are only provided as examples. Alternatively or additionally, user interface element may provide a graphical representation of the spine (including estimated relative position between the vertebra based on the alignment measurement) which may be a model based on pre-operative or intra-operative CT data and updated based on the sensor readings. The visualization may be presented in an augmented reality fashion by overlaying it on the actual view of the surgeon either on a fixed monitor or a wearable display such as augmented reality or mixed reality googles/glasses.

Processes and methods consistent with the disclosed embodiments have been described in accordance with specific orthopedic procedures, namely a spine surgical procedure. Those skilled in the art will recognize, however, that these descriptions were exemplary only, and that the presently disclosed anatomic orientation measurement system can be used in most any situation in which surgical precision is important. Indeed, although certain embodiments were described with respect to tracking placement of a spine, it is contemplated that such methods and systems are equally applicable to other anatomies, such as hips, knees, and shoulders.

Figure 8:
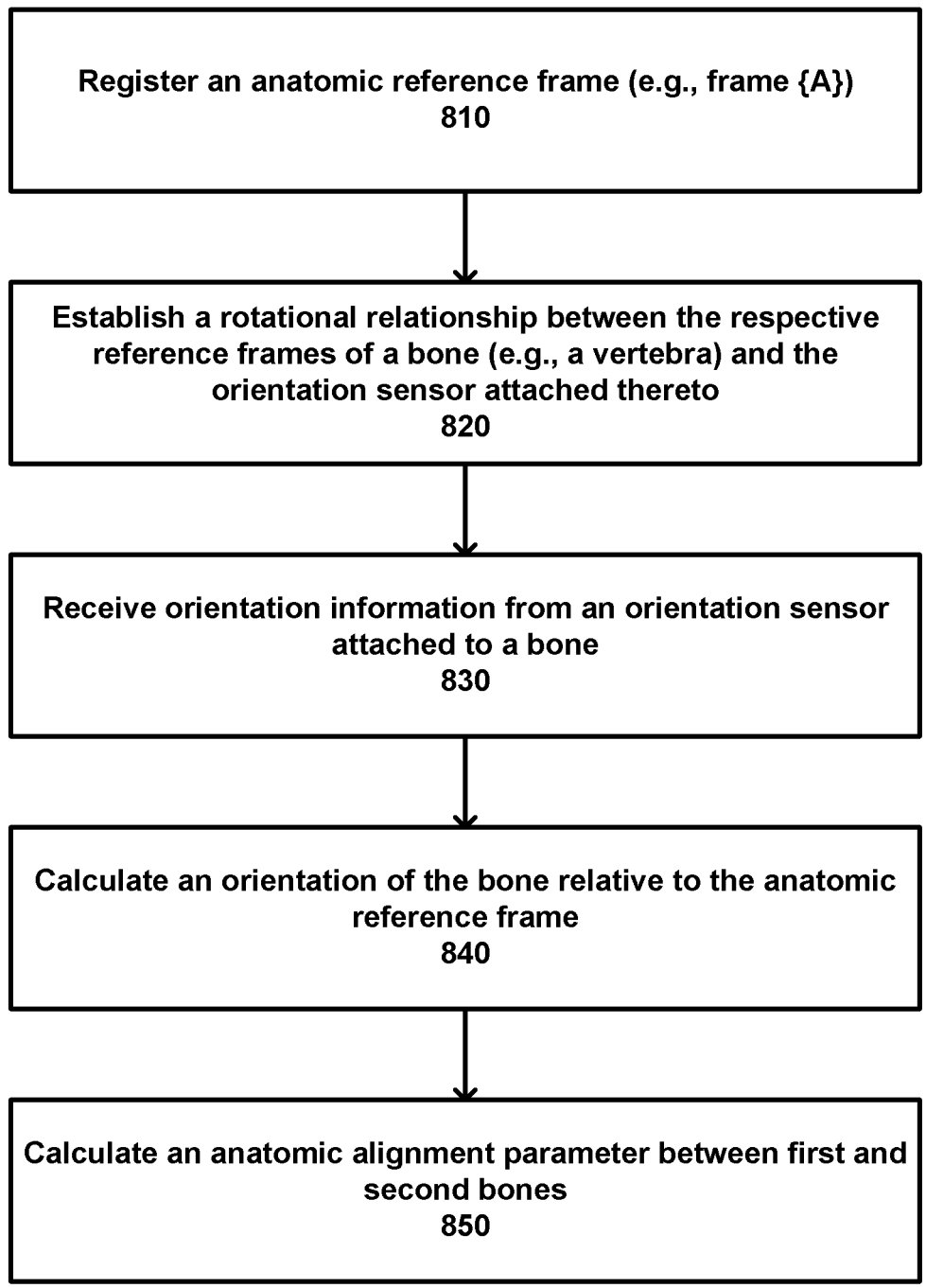
FIG. 8 is a flowchart illustrating an example process to be performed by one or more processing devices associated with an example anatomic orientation measurement system according to implementations described herein.

Referring now to FIG. 8, a flowchart illustrating an example process to be performed by one or more processing devices associated with an example anatomic orientation measurement system is shown. This disclosure contemplates that the operations can be performed by the system 300 shown in FIGS. 2 and 3, for example. At 810, the process includes registering an anatomic reference frame (e.g., frame {A} in FIG. 4). As described herein, the global reference (e.g., global reference frame {G} in FIG. 4A) frame can optionally be defined by the NED convention used by inertial navigation sensor. The global reference frame, however, is not limited by this definition and can be another locally or globally defined frame. The registration information (e.g., relationship $^{G}R_{A}$ in FIG. 4A) can be stored in memory of a processing system (e.g., processing and display unit 350 in FIGS. 2 and 3). It should be understood that relationship $^{G}R_{A}$ can be used to convert orientation information measured by the orientation sensor relative to the global reference frame into a measurement relative to the anatomic reference frame. Optionally, the process can include establishing and storing a common global reference frame in the case when more than one orientation sensor is used. As described above, this can be achieved by calibrating/zeroing the orientation sensors in a zeroing or alignment tray prior to use, where the processing system "zeroes" out the differences in the individual global reference frames. Example anatomic registration techniques are described above with regard to FIGS. 5A and 5B. For example, anatomic registration can be achieved by palpating two or more anatomic landmarks such as the PSIS or any other landmark or combination thereof as described with reference to FIG. 5A. Alternatively, kinematic methods can be utilized as described with reference to FIG. 5B.

Following anatomic registration, at step 820, the process include establishing a rotational relationship between the respective reference frames of a bone (e.g., a vertebra) and the orientation sensor attached thereto. For example, in FIG. 4A, the orientation sensor 340 is attached to a vertebra (e.g., a bone). The orientation sensor's reference frame is shown by $\{S\}$, and the bone's reference frame is shown by $\{V\}$. The rotational relationship between frames $\{V\}$ and $\{S\}$ is shown by relationship $^{V}R_{S}$ in FIG. 4A. The step is particularly important when the bone (e.g., a vertebra) is at an arbitrary unknown orientation with respect the anatomic reference frame and/or the sensor reference frame. Several methods are available to establish the rotational relationship ranging from mechanical, imaging-based and/or manual. For example, techniques for establishing a rotational relationship are described above with regard to FIGS. 6A and 6B. The rotational relationship information (e.g., relationship $^{V}R_{S}$ in FIG. 4A) can be stored in memory of a processing system (e.g., processing and display unit 350 in FIGS. 2 and 3). It should be understood that relationship $^{V}R_{S}$ can be used to convert orientation information measured relative to the anatomic reference frame (e.g., measured by an orientation sensor relative to the global reference frame and then converted to the anatomic reference frame using relationship $^{G}R_{A}$) into a measure of the bone's orientation relative to the anatomic reference frame. This disclosure contemplates that step 820 can be performed for each of a plurality of bones (e.g., first and second bones such as two different vertebrae). In some implementations, an orientation sensor is attached only to the one or more bones expected to move during surgery, e.g., when at least one second bone is not expected to move during surgery as described above. In these implementations, the orientation sensor(s) need only be attached to the bone(s) that are expected to move during surgery, while the angle of the at least one second bone is measured relative to an anatomic plane of interest, for example, during the registration process. In other implementations, a respective orientation sensor is attached to each of at least two bones, and the rotational relationship calculated in step 820 is calculated for each bone.

Once the above rotational relationships are established, at step 830, the process can include receiving orientation information from an orientation sensor attached to a bone. This disclosure contemplates that the bone can be a vertebra in the patient's spine in some implementations. It should be understood, however, that the bone is not limited to a vertebra and can be another bone of the patient's anatomy. As described above, the orientation sensor (e.g., orientation sensor 340) measures orientation relative to a global reference frame (e.g., frame $\{G\}$ in FIG. 4A), which can be converted to a measurement relative to an anatomic reference frame (e.g., frame $\{A\}$ in FIG. 4A) using relationship $^{G}R_{A}$. At step 840, the process can include calculating an orientation of the bone relative to the anatomic reference frame. This can be accomplished using relationship $^{V}R_{S}$, which relates the orientation sensor's frame to the reference frame of the bone. The respective orientations of the orientations sensors and/or bones can be stored in memory of a processing system (e.g., processing and display unit 350 in FIGS. 2 and 3). This disclosure contemplates that steps 830 and 840 can be performed for each of a plurality of bones (e.g., first and second bones such as two different vertebrae).

At 850, the process can include calculating an anatomic alignment parameter between first and second bones (e.g., two vertebrae). For example if $a_{vi}$ is orientation of bone "i" in the anatomic reference plane and $a_{vj}$ is orientation of bone "j" in the same plane, then $a_{vj}-a_{vi}$ is the relative orientation or alignment between the bones in the anatomic reference plane. As described herein, the anatomic alignment parameter can be a joint angle, a spine alignment angle, or other alignment parameter. This calculation can be based on the respective orientations of the first and second bones relative to the anatomic reference frame calculated in step 840. Optionally, the process can include displaying the anatomic alignment parameter on a display device (e.g., display 358a in FIG. 3), for example, as shown by the display in FIG. 7. Additionally, this disclosure contemplates that the process shown in FIG. 8 can be performed in real time during a surgical procedure (e.g., intra-operatively).

It will be apparent to those skilled in the art that various modifications and variations can be made to the disclosed systems and methods for measuring orthopedic parameters associated with a reconstructed joint in orthopedic arthroplastic procedures. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method for estimating anatomic alignment between two or more bones, comprising:
   receiving, via a first orientation sensor; first information indicative of an orientation of an anatomic axis or plane relative to a global reference frame;
   registering, using the first information, an anatomic reference frame;
   establishing a rotational relationship between the anatomic reference frame of a second orientation sensor attached to a first bone and the first bone;
   receiving, via the second orientation sensor attached to the first bone, second information indicative of an orientation of the second orientation sensor attached to the first bone;
   calculating, using the registered anatomic reference frame, the second information, and the rotational relationship, an orientation of the first bone relative to the anatomic reference frame; and
   calculating, using the orientation of the first bone relative to the anatomic reference frame, an anatomic alignment parameter between the first bone and at least one second bone.

2. The method of claim 1, further comprising receiving an angle of the at least one second bone measured in an anatomic plane of interest.

3. The method of claim 1, further comprising:
establishing a respective rotational relationship between at least one second bone and respective reference frames of a respective orientation sensor attached to the at least one second bone;
receiving, via each of the respective orientation sensors attached to the at least one second bone, third information indicative of a respective orientation of each of the respective orientation sensors attached to the at least one second bone; calculating, using the registered anatomic reference frame, the third information, and the respective rotational relationships, a respective orientation of each of the at least one second bone relative to the anatomic reference frame, wherein the anatomic alignment parameter between the first bone and the at least one second bone are calculated using respective orientations of the first bone and the at least one second bone relative to the anatomic reference frame.

4. The method of claim 1, wherein registering the anatomic reference frame comprises palpating one or more anatomic landmarks with a tool comprising the first orientation sensor.

5. The method of claim 1, wherein registering the anatomic reference frame comprises performing kinematic registration with the second orientation sensor.

6. The method of claim 1, further comprising calibrating/zeroing the first orientation sensor and the second orientation sensor attached to the first bone to establish a common global reference frame.

7. The method of claim 1, wherein establishing the rotational relationship between the anatomic reference frame of the second orientation sensor attached to the first bone and the first bone comprises using a mechanical instrument to align the first orientation sensor in a known orientation relative to the first bone.

8. The method of claim 1, wherein establishing the rotational relationship between the anatomic reference frame of the second orientation sensor attached to the first bone and the first bone comprises using an image of the first bone with the second orientation sensor attached to the first bone.

9. The method of claim 1, wherein establishing the rotational relationship between the anatomic reference frame of the second orientation sensor attached to the first bone and the first bone comprises deriving the rotational relationship based on respective rotational relationships between the anatomic reference frames of the second orientation sensor attached to the first bone and the first bone relative to the anatomic reference frame.

10. The method of claim 1, wherein the anatomic axis or plane is at least one of a sagittal, coronal, or transverse plane.

11. The method of claim 1, wherein the anatomic axis or plane is a plane parallel to at least one of a sagittal, coronal, or transverse plane.

12. The method of claim 1, wherein the anatomic axis or plane is parallel to at least one of a longitudinal, transverse, or frontal axis.

13. The method of claim 1, wherein the anatomic reference frame is specific to a certain portion of a patient's anatomy identified by bony landmarks.

14. The method of claim 1, further comprising displaying the anatomic alignment parameter between the first bone and the at least one second bone on a display device.

15. The method of claim 1, wherein the anatomic alignment parameter is a joint angle or a spine alignment angle.

16. A system for estimating anatomic alignment between two or more bones, the system comprising:
an elongated tool having first and second ends;
a first orientation sensor coupled to the elongated tool;
a second orientation sensor configured to be coupled to a first bone;
a processor, communicatively coupled to the first and second orientation sensors and configured to:
receive, via the first orientation sensor, first information indicative of an orientation of an anatomic axis or plane relative to a global reference frame;
register, using the first information, an anatomic reference frame;
establish a rotational relationship between the anatomic reference frame of the second orientation sensor and the first bone;
receive, via the second orientation sensor, second information indicative of an orientation of the second orientation sensor;
calculate, using the registered anatomic reference frame, the second information, and the rotational relationship, an orientation of the first bone relative to the anatomic reference frame; and
calculate, using the orientation of the first bone relative to the anatomic reference frame, an anatomic alignment parameter between the first bone and at least one second bone.

17. The system of claim 16, wherein the first and second orientation sensors are the same sensor.

18. The system of claim 16, wherein the first and second orientation sensors are different sensors.

19. The system of claim 16, wherein the processor is further configured to receive an angle of the at least one second bone measured in an anatomic plane of interest.

20. The system of claim 16, further comprising a respective orientation sensor attached to at least one second bone, the processor being further configured to:
establish a respective rotational relationship between the at least one second bone and respective reference frames of the respective orientation sensor attached to the at least one second bone;
receive, via each of the respective orientation sensors attached to the at least one second bone, third information indicative of a respective orientation of each of the respective orientation sensors attached to the at least one second bone;
calculate, using the registered anatomic reference frame, the third information, and the respective rotational relationships, a respective orientation of each of the at least one second bone relative to the anatomic reference frame, wherein the anatomic alignment parameter between the first bone and the at least one second bone are calculated using respective orientations of the first bone and the at least one second bone relative to the anatomic reference frame.

21. The system of claim 16, further comprising:
a first pointer coupled to the elongated tool and configured to provide an offset between a first portion and the first end; and
a second pointer coupled to the elongated tool and configured to provide an offset between a second portion and the second end.

22. The system of claim 21, wherein lengths of the first pointer and the second pointer provide a substantially uniform offset at the first end and the second end.

23. The system of claim 21, wherein at least one of the first or second pointers is slidably coupled to an elongated linear member, such that distance between the first pointer and the second pointer is adjustable.

24. The system of claim 16, further comprising a display device, wherein the processor is further configured to cause display of the anatomic alignment parameter between the first bone and the at least one second bone on the display device.

25. The system of claim 16, wherein the first or second orientation sensor is an inertial measurement unit that includes at least one of a gyroscope, an accelerometer, or a magnetometer.

26. The system of claim 16, wherein the first or second orientation sensor is an inertial measurement unit that includes a gyroscope and an accelerometer.

27. The system of claim 16, wherein the anatomic alignment parameter is a joint angle or a spine alignment angle.

* * * * *